United States Patent [19]

Uematsu et al.

[11] Patent Number: 5,144,951
[45] Date of Patent: Sep. 8, 1992

[54] APPARATUS FOR MEASURING BIOPERMEABILITY

[75] Inventors: Kazuma Uematsu, Tokyo; Shigehiro Kinoshita, No. 628-2, Nishifukai, Nagareyama-shi, Chiba; Kazuo Tsuji, No. 18-30, Osawa 4-chome, Mitaka-shi, Tokyo, all of Japan

[73] Assignees: Macttor Co., Ltd., Tokyo; Shigehiro Kinoshita, Chiba; Kazuo Tsuji, Tokyo, all of Japan

[21] Appl. No.: 825,323

[22] Filed: Jan. 27, 1992

Related U.S. Application Data

[63] Continuation of Ser. No. 488,895, Mar. 6, 1990, abandoned.

[30] Foreign Application Priority Data

Mar. 9, 1989 [JP] Japan .................................. 1-58251

[51] Int. Cl.$^5$ .............................................. A61B 5/00
[52] U.S. Cl. .................................. 128/633; 128/665; 356/41
[58] Field of Search .................... 128/633, 664–666; 356/41

[56] References Cited

U.S. PATENT DOCUMENTS

| | | | |
|---|---|---|---|
| 3,522,739 | 8/1970 | Coor | 356/41 |
| 3,998,550 | 12/1976 | Koniski | 356/41 |
| 4,407,290 | 10/1983 | Wilber | 128/633 |
| 4,603,700 | 8/1986 | Nichols | 356/41 |
| 4,655,225 | 4/1987 | Dahne | 128/633 |
| 4,800,885 | 1/1989 | Johnson | 356/41 |
| 4,807,630 | 2/1989 | Malinouskas | 128/633 |
| 4,819,752 | 4/1989 | Zelin | 356/41 |
| 4,824,242 | 4/1989 | Frick | 128/633 |
| 4,846,183 | 7/1989 | Martin | 356/41 |
| 4,867,165 | 9/1989 | Noller | 128/633 |
| 4,869,253 | 9/1989 | Craig | 128/633 |
| 4,907,876 | 3/1990 | Suzuki | 128/633 |
| 4,927,264 | 5/1990 | Shiga | 128/633 |

FOREIGN PATENT DOCUMENTS

| | | |
|---|---|---|
| 1541765 | 10/1972 | Fed. Rep. of Germany . |
| 2727138 | 12/1977 | Fed. Rep. of Germany . |
| 3040831 | 7/1982 | Fed. Rep. of Germany . |
| 3135443 | 9/1988 | Fed. Rep. of Germany . |
| 2065878 | 7/1981 | United Kingdom . |
| 2105461 | 3/1983 | United Kingdom . |

*Primary Examiner*—Ruth S. Smith
*Assistant Examiner*—R. L. Nusser
*Attorney, Agent, or Firm*—Pollock, VandeSande & Priddy

[57] ABSTRACT

An apparatus for measuring biopermeability is disclosed. The apparatus includes a frame, a light source, a light-receiving element, a pre-amplifier, an off-set adjustment amplifier and a DC volt meter. The light source and light-receiving element are secured to the frame such that they face each other while keeping a gap therebetween such that an organism under measurement can be received in the gap without being urged. The pre-amplifier is connected to the light-receiving element and has a gain switching function. The summing amplifier is connected for zero adjustment and gain adjustment to the output side of the pre-amplifier and has an output terminal from which a DC data representing biopermeability is provided. Between the output terminal and ground the DC volt meter is connected.

7 Claims, 2 Drawing Sheets

APPARATUS FOR MEASURING BIOPERMEABILITY

This application is a continuation of Ser. No. 07/488,895 filed on Mar. 6, 1990, now abandoned.

BACKGROUND OF THE INVENTION

1. Field of the Invention

This invention relates to an apparatus for measuring biopermeability.

2. Statement of the Prior Art

The technology of biopermeability measurement is extensively utilized for photoelectric plethysmographs (finger tip volume sphygmographs) and the like. The photoelectric plethysmograph utilizes the facts that blood in capillaries abundantly present in subcutaneous tissues of the finger tip or the like absorbs red light very well and that volumetric variations of blood vessels cause permeability variations.

The volumetric variations of blood vessels correspond to variations of blood flow for the following reasons. The absolute value of permeability is determined by the optical absorbence and physical quantity of matter located in the position of measurement. Therefore, the measured value of permeability reflects the volumes of tissues and blood of an organism occupying a measurement zone. This is why the volumetric variations of blood vessels correspond to variations of blood flow.

Further, the volume of a blood vessel is proportional to the sectional area thereof. Generally, the waveform of a photoelectric plethysmograph reflects variations of the sectional area of the vessel. Variations of the sectional area of the vessel result from expansion and contraction of vessel membrane due to variations in the pressure in the vessel. Therefore, the waveform of a photoelectric plethysmograph is determined by blood pressure variations in the vessel and by expansibility of the vessel membrane with respect to blood pressure. The blood pressure is collectively influenced by the force which forces blood out from the heart, volume of vessel, elasticity-characteristics of the vessel membrane, vein pressure and tension in the smooth muscles present in the vessel membrane. These four factors have a complex reflection on the blood pressure waveform. If these factors deviate from their normal values due to various disease causes, characteristic changes are produced in the waveform. The waveform change pattern is used for diagnosis through pattern recognition technique.

The force which forces blood out of the heart, as noted above, refers to the capacity of the heart as a source of energy to force out blood to the aorta, and the volume of the vessel refers to the inner volume of the aorta viewed from the heart.

Prior art biopermeability measurement apparatus does not measure absolute permeability, and therefore has a simple construction of a light source and a photo-sensor. The biopermeability to light is usually very low, specifically about 1% or below. Besides, variation of the vessel volume from average vessel volume due to blood pressure variation is also low. Therefore, in order to ensure sufficient signal-to-noise ratio in the measurement, the biopermeability to light and range thereof have to be measured with a sensor section urged against the surface of the organism under measurement that is, in a state in which the vessel membrane is adequately squeezed by external pressure to increase volume changes. The urging of the locality of measurement does not only increase the amplitude of volume change component in the vessel but also helps keep stable the coupling of optical system and organism to each other, thus contributing to the stability of the base line of the waveform of measurement. Therefore, the optical system may be of a simple construction including only a light source and a light-receiving element, and a high performance sensor is not necessary.

In the prior art biopermeability measurement apparatus, however, usually the base line of the recording is stabilized, and therefore the sensor output signal is AC amplitude by an amplifier having a time constant on the order of 1.6 sec. This means that only a change in light transmitted through the organism is recorded, and also it is difficult to obtain a stable setting of a 100% light incidence state, i.e., a state of 100% incidence of light flux from a light source on a light-receiving element, which state is used as reference in the measurement of biopermeability. Therefore, calibration of absolute permeability is impossible. For this reason, the output of the prior art apparatus is irrelevant to the absolute value of permeability even though it may represent permeability variation, and therefore it is designed on the basis of a gain (or amplification degree) selected at the manufacturer's convenience. It is thus impossible to compare amplitude data obtained by measurements with different apparatuses, and comparison of measurements is most often done with respect to waveform patterns. Although data obtained with the same kind of apparatus can be compared, even such comparison is meaningless unless the individual apparatuses are calibrated.

Further, about two-thirds of the blood pressure data is constituted by average value as DC component, and the variation data constitutes only about one-third of the overall data. The average blood pressure value as DC component contains various data. Nevertheless, where the photo-sensor mounting structure is of pressure application type, measurement is done in a state in which the vessel volume is slightly reduced under external pressure because of the external pressure being applied to the vessel membrane by the urging of the same when the photo-sensor is mounted. In addition, the measuring condition varies with the extent of urging, which in turn varies for every measurement. Therefore, it is extremely difficult to obtain measurement under fixed conditions. This means that it is inevitable to use only the change component of measurement. What is more, even the change component is greatly influenced by changes in the external pressure due to urging which results in changes in the waveform pattern. This is a grave defect in that it causes erroneous diagnosis.

The present invention intends to overcome the above drawbacks inherent in the prior art biopermeability measurement apparatus, and its object, accordingly, is to provide a biopermeability measurement apparatus which permits continuous and accurate measurement of the absolute value of permeability to light transmitted through an organism under measurement even if the transmitted light has very weak intensity.

Another object of the invention is to provide a biopermeability measurement apparatus which permits automatic measurement of the absolute value of biopermeability.

SUMMARY OF THE INVENTION

To attain the above first object, in one aspect of the invention there is provided an apparatus for measuring biopermeability, which comprises a frame, a light source and a light-receiving element both secured to the frame such that they face each other while keeping a gap between them such that an organism under measurement can be received in the gap without being urged, a pre-amplifier connected to the light-receiving element and having a gain switching function, an offset adjustment amplifier connected for zero adjustment and gain adjustment to the output side of the pre-amplifier and having a DC output terminal, the DC output data representing biopermeability being provided from an output terminal, and a DC volt meter connected between the output terminal and ground.

With this construction, it is possible to measure permeability by receiving an organism without its being urged, and hence the measurement may be done under a condition not producing any strain in the blood vessel. Thus, variation data of the organism can be obtained accurately by eliminating the influence of external pressure.

In addition, since the degree of amplification can be switched between high and low for taking out the light-receiving element output, even at the 100% light reception in a low amplification degree mode, the absolute value of permeability can be calibrated accurately without considering saturation of the succeeding stage amplifier, and it can be measured continuously in a high amplification degree mode in the actual measurement.

Further, since the apparatus itself has a calibrating function, calibration can be effected whenever reduction of sensitivity results from contamination of the optical system in long use.

In a preferred mode of the invention, the frame is a metal frame having high mechanical strength.

In a further preferred mode of the invention, the light source is either a gas laser, a semiconductor light-emitting element or a lamp.

In a still further preferred mode of the invention, the light source is a high brightness red light-emitting diode.

In a yet further preferred mode of the invention, the light-receiving element is a photo-diode.

In a further preferred mode of the invention, the receiving element has a light incidence surface having an area capable of receiving the entire light flux emitted from the light source and incident through the organism under measurement.

In a further preferred mode of the invention, if the light flux emitted from the light source is not a parallel light flux, an optical system is disposed between the light source and the organism under measurement for converting the emitted light flux to a parallel light flux.

In a further preferred mode of the invention, the pre-amplifier is an operational amplifier having two different gains capable of being selected by switching, the two gains being unity and 100 times unity.

In a further preferred mode of the invention, the off-set adjustment amplifier includes a zero adjuster and an amplification degree adjuster. The amplification degree adjuster preferably includes a gains adjuster and an operational amplifier.

In a further preferred mode of the invention, the DC potentiometer is of a 10 volt full scale, the zero adjuster is adjusted such that the DC potentiometer indicates 0 volt when permeability that is measured is 0%, and the amplification degree adjuster is adjusted such that the DC potentiometer indicates 10 volts when permeability measured is 100%.

In a further preferred mode of the invention, an AC inverting amplifier circuit is connected to an output terminal, the AC inverting amplifier circuit suitably including a CR coupler and an amplifier having a fixed amplification factor and providing AC output data.

With the light-receiving element output amplified through the DC amplifier to obtain a DC output and also amplified through an AC amplifier to obtain an AC output, it is possible to obtain permeability absolute value data from the DC output and also permeability variation data from the AC output.

In this case, the fixed amplification factor is suitably set to 50.

Preferably, the inverting amplifier circuit includes an inverting amplifier connected to the output terminal of the fixed amplification factor amplifier and having an output terminal providing AC data.

The inverting amplifier suitably has a unity amplification factor.

Further, a switch is suitably provided between the CR coupler and the fixed amplification factor amplifier such that the switch is operable to cause discharge of the capacitor so as to correct the base line of the measurement waveform to zero.

Further, according to the invention a data processing unit may be provided which includes an A/D converter for converting the DC and AC output data into respective digital DC and AC data, a DSP sub-unit for performing frequency analysis of DC and AC output data from the A/D converter, a memory for storing waveform data and frequency spectra data obtained from the DSP sub-unit, a display sub-unit for displaying the waveform data and frequency spectra data, and a control sub-unit for controlling operation of the data processing unit.

With this arrangement, permeability data may be automatically processed by a computer in the data processing unit for displaying effective data for diagnosis.

BRIEF DESCRIPTION OF THE DRAWINGS

Foregoing and other objects and advantages of the present invention will be better understood by reference to the description, taken in connection with the accompanying drawings, in which.

DETAILED DESCRIPTION OF THE PREFERRED EMBODIMENTS

An embodiment of the apparatus for measuring biopermeability according to the invention will be described in detail with reference to the drawings.

Figure 1:
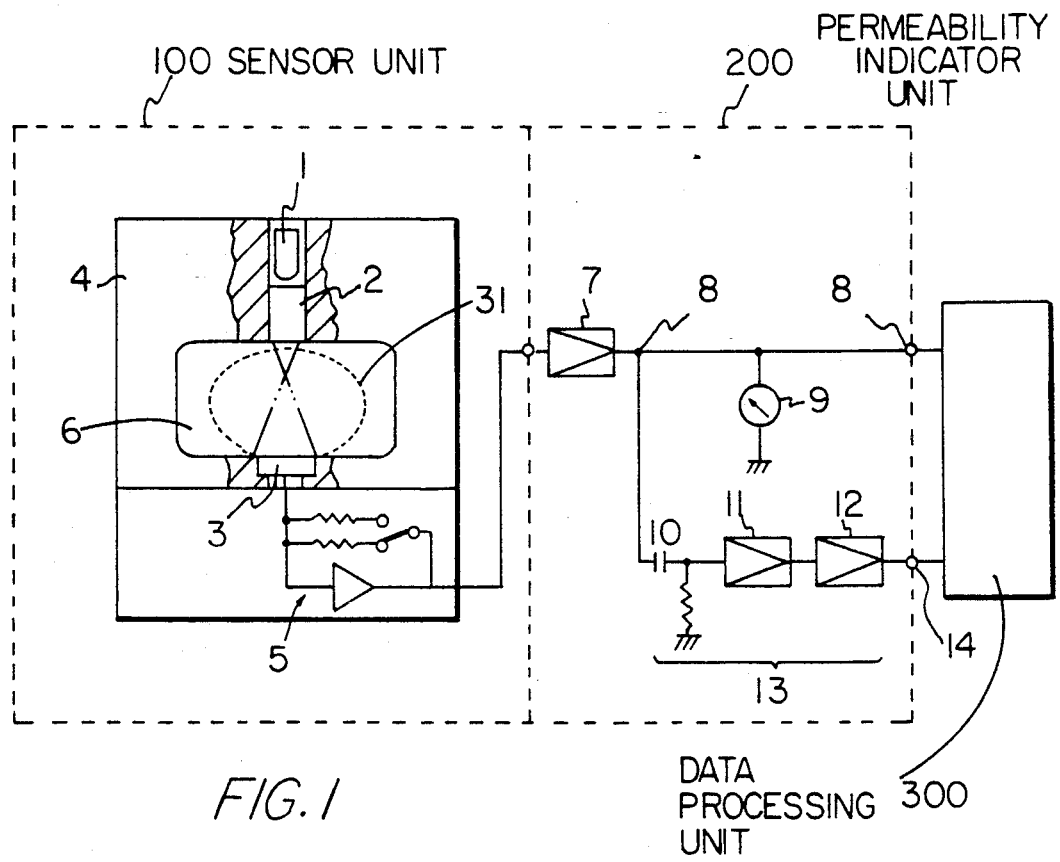
FIG. 1 is a schematic diagram, including a partially cutaway view of a sensor unit, showing a preferred embodiment of the biopermeability measurement apparatus according to the present invention.

FIG. 1 shows a preferred embodiment of the biopermeability measurement apparatus according to the invention. As shown, the apparatus comprises sensor unit 100 and permeability indicator unit 200. Data processing unit 300 using a microcomputer may be connected to permeability indicator unit 200 to permit automatic data processing.

Sensor unit 100 includes a light projection section having a light source 1 and an optical system 2 including a lens system, a light-receiving element 3, a metal frame 4 supporting the above components and a pre-amplifier 5 of unity/100 times gain switching type. Metal frame 4 has sufficient mechanical strength to eventually suppress mechanical vibrations. In metal frame 4, measuring section 6 is provided, by a space, for instance a through hole sufficiently greater, for instance by the order of several millimeters, than the outer diameter of an organism 31 under measurement organism 31 may for instance be a finger. Measuring section 6 is defined by an angular loop wall, on the inner surface of which light-receiving element 3 is secured such that a light incidence surface thereof is substantially flush with the inner surface of measuring section 6. Light source 1 is disposed to face light-receiving element 3 either directly, or if necessary via optical system 2 such that its emitted light flux substantially coincides with the entire light incidence surface of light-receiving element 3. With this arrangement, the emitted light flux may be substantially 100% incident on the light-receiving element. Light source 1 may emit light of any desired wavelength. A high brightness red light-emitting diode is suitable as light source 1, but where stability and light intensity are sufficient, a gas laser, a semiconductor laser or a lamp with a red filter may also suitably be used. Optical system 2 desirably uses a converting rod lens of an optical fiber such that the diameter of light flux incident on organism 31 under measurement is as small as about 1 millimeter. No lens, however, is necessary in the case where light source 1 emits a parallel (or coherent) light beam such as a laser beam. When light is incident on it, light-receiving element 3 produces a corresponding output current, which is converted to voltage by pre-amplifier 5. Pre-amplifier 5 suitably serves as an operational amplifier capable of switching gain between unity and 100.

A photodiode may be used for light-receiving element 3. But where sufficient spectral characteristics and signal-to-noise ratio are obtainable, other semiconductor light-receiving elements may be used as well. Further, the light-receiving element 3 suitably has a small light incidence surface. However, if the light incidence surface is too small, the output is reduced to the extent that the signal-to-noise ratio deteriorates. Therefore, an adequate light incidence area is necessary. A practical size of the area is 2 to 3 millimeters in diameter, but it be important that the area is virtually the same size as the diameter of the light flux from light source 1. Metal frame 4 desirably has a large size and is made of a metal having satisfactory heat conductivity, for instance, aluminum, for the purpose of dissipating heat generated by light source 1.

Figure 2:
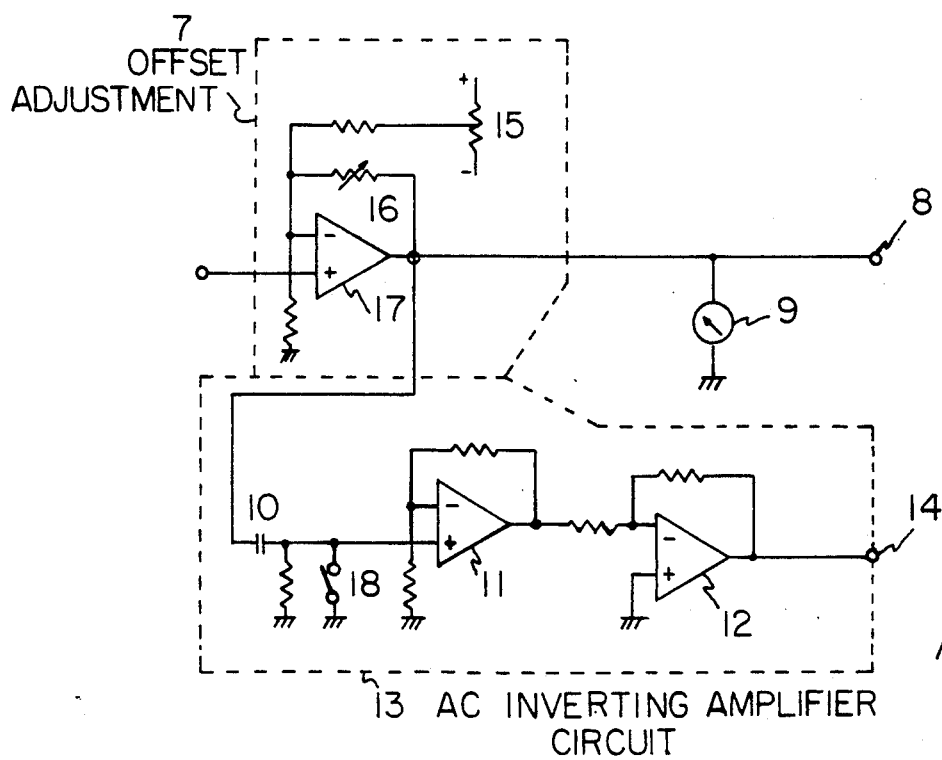
FIG. 2 is a circuit diagram of a permeability indicator unit consisting of a portion of the biopermeability measurement apparatus according to the present invention.

Permeability indicator unit 200 includes an offset adjustment amplifier 7 and a DC volt meter 9. Off-set adjustment amplifier 7, as shown in FIGS. 1 and 2, has an off-set adjustment circuit which permits adjustment of the output to 0 V when the permeability is 0%, and an amplification adjustment circuit for setting the output to 10 V at 100% permeability. DC volt meter 9 is 10-V at full scale and is connected to DC output terminal 8 of off-set adjustment amplifier 7.

Connected, too, to DC output terminal 8 is AC inverting amplifier circuit 13, which includes CR coupler 10, an amplifier 11 with a fixed amplification factor of 50, for instance, and an inverting amplifier 12 with a unity amplification factor, so that an AC output voltage inverted in phase is obtained from output terminal 14. Phase inversion facilitates waveform comparison. Off-set adjustment amplifier 7, as shown in detail in FIG. 2, includes a zero adjuster 15 consisting of an off-set adjustment potentiometer and an operational amplifier 17 with sensitivity adjuster 16 consisting of a feed-back resistor for amplification degree adjustment.

Switch 18 is connected to the output side of CR coupler 10 to permit, when desired, the discharging of the capacitor in CR coupler 10 to correct the base line of measurement waveform to zero.

The operation of the permeability measurement apparatus having the above construction according to the invention will be described.

Before using the apparatus, a calibrating operation is necessary for setting DC amplification gains for 0 and 100% permeabilities.

First, pre-amplifier 5 in sensor unit 100 is set at unity gain with the switch provided in the pre-amplifier. In this state, light-receiving element 3 is covered with a metal plate or similar light-blocking plate so that light from light source 1 will not be incident on light-receiving element 3. In this 0% permeability state, zero adjuster 15 is adjusted to adjust the reading of volt meter 9 to 0 volt. Subsequently, the light-blocking plate covering light-receiving element 3 is removed to let light from light source 1 be directly incident onto light-receiving element 3. In this state, i.e., at 100% permeability gain adjuster 16 is adjusted to adjust the reading of volt meter 9 to 10 volts. With these adjustments, the gain of off-set adjustment amplifier 7 is accurately adjusted to 10% permeability per volt.

Subsequent to the above gain adjustment, pre-amplifier 5 in sensor unit 100 is switched to the 100 gain mode, in which the output of off-set adjustment amplifier 7 represents 0.1% permeability per volt. In this mode, light-receiving element 3 is covered to provide 0% permeability. In this state, zero adjuster 15 is adjusted such that the reading of DC volt meter 9 represents 0 volt. With this second adjustment, an error in the previous first zero adjustment is removed by fine adjustment, thus completing the calibration of the apparatus.

The unity amplification degree adjustment adjusts the DC sensitivity of the measuring system, and the 100% amplifying gain adjustment the zero adjustment. The 100 times gain mode is a biomeasurement mode with a measurement range of 0 to 1%. However, the absolute value of permeability when measuring a finger of a person is about 0.2 to 0.4%, and this means that the measurement range of 0 to 1% is adequate. When the fixed amplification factor of AC inverting amplifier circuit 13 is selected to be 50, the amplitude of the AC output is calibrated to permeability variation of 0.002% per volt.

In actual measurement, after completion of calibration process described above, as organism 31 under measurement such as a finger is inserted into measuring section 6 in sensor unit 100 with the surface of one side of the finger being in close contact with the light incidence surface of light-receiving element 3, as shown in FIG. 1. Light from light source 1 is partly transmitted through organism 31 under measurement to impinge on light-receiving element 3. Thus, the variable blood flow through the finger blood capillaries can be measured as a corresponding electric signal. At the time of the measurement, the measuring section is of course covered for blocking external light.

In permeability indicator unit 200, the permeability and variations thereof can be directly read from DC volt meter 9. Further, continuous changes in permeability are provided as corresponding voltage changes from DC and AC output terminals 8 and 14. These output data may be recorded as waveforms in an analog recorder, for instance. In addition, they may be converted by an A/D converter into digital time-serial data to be supplied to a microcomputer for data processing, display of the results of processing and storing. These data may be used for diagnosis and prevention of various diseases.

Figure 3:
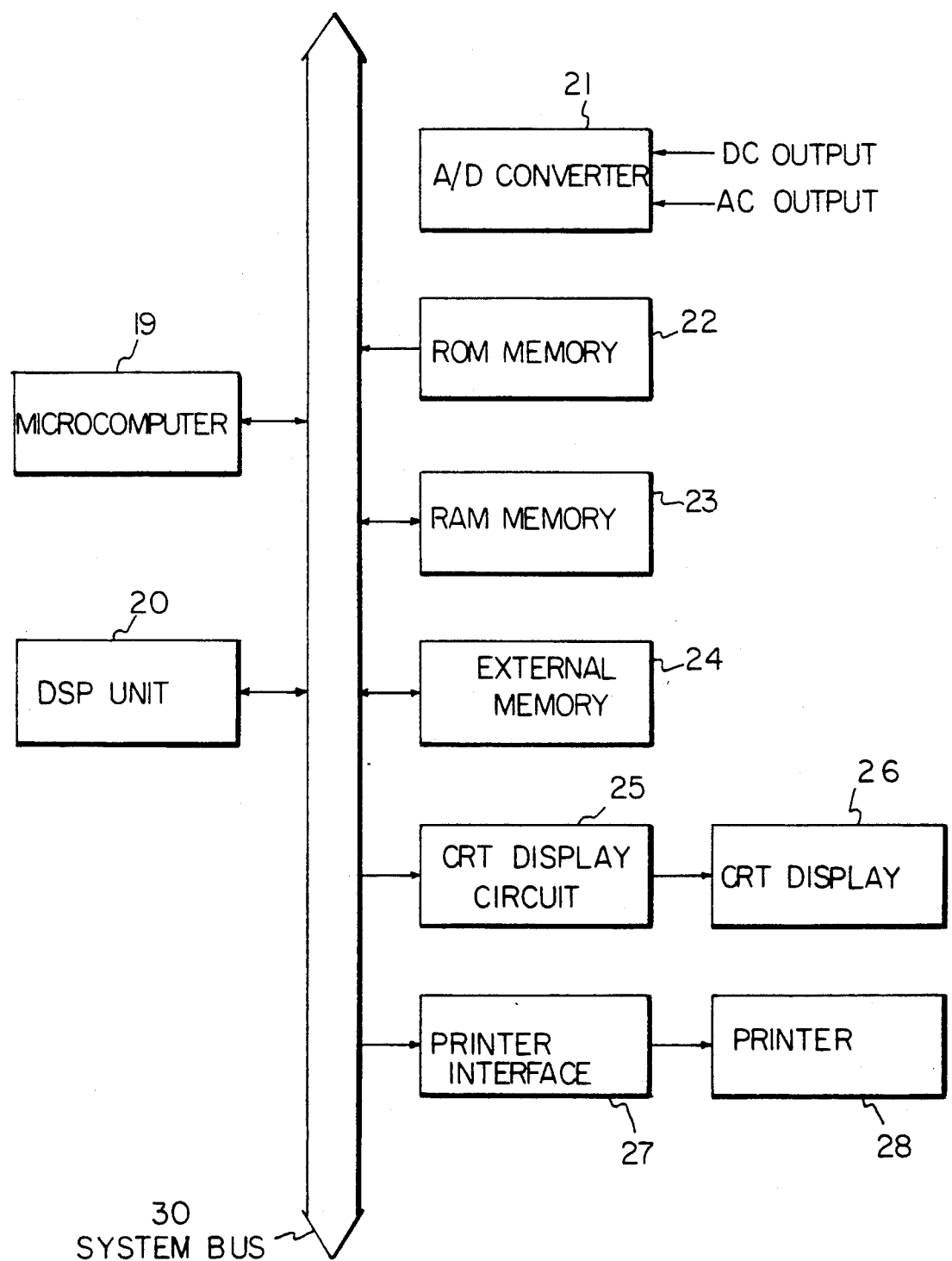
FIG. 3 is a block diagram of a data processing unit consisting, if desired of, a portion of the biopermeability measurement apparatus according to the present invention.

FIG. 3 shows in a simplified block diagram an example of data processing unit 300. As shown, microcomputer 19, DSP (digital signal processor) unit 20, A/D converter 21, ROM memory 22, RAM memory 23, external memory 24, CRT display circuit 25, CRT display 26, printer interface 27 and printer 28 are provided connected to system bus 30, and the outputs from DC and AC output terminals 8 and 14 are provided to A/D converter 21.

In data processing unit 300, frequency analysis is performed by calculation method that adopts an FFT algorithm or a self-restoration model (proposed by Hirotsugi Akaji in the Statistical Mathematic Theory Research Institute, the Ministry of Education, 1969). In the calculating process, DSP unit 20 effects real-time frequency analysis and display. As a result, waveform and frequency spectrum data are displayed on CRT display 26, and the resulting output is printed on printer 28. Further, necessary digital data is stored in external memory 24. The above data processing is performed according to programs worked out in advance in external memory 24 or ROM memory 22 capable of frequency analysis and data display and storage. Microcomputer 19 constitutes a control section of data processing unit 300 and may be comprised of a universal personal computer. Alternatively, an exclusive computer for data processing may be constructed by combining LSIs of CPU, a RAM, a ROM and I/O.

According to the invention as described in the foregoing, the following advances are obtained.

Since permeability is measured by receiving an organism under measurement in a non-urged state, it is possible to eliminate waveform distortions due to urging of the organism and permit measurement of biopermeability under constant conditions at all times. In other words, the measured results for every measurement do not vary, and accurate measured results can be obtained at all times. Thus, there is no possibility that erroneous diagnosis results from a change in waveform as a result of measurement due to the extent of urging, and it is possible to compare results of measurements performed with different times or with different apparatuses of measurement.

Further, the output current from the light-receiving element is coupled to a pre-amplifier having a gain switching function so that it can be provided with one of suitably two, i.e., high and low, switchable gains, while permitting zero adjustment and gain adjustment in the subsequent amplifier circuit. Thus, accurate calibration of the absolute value of 100% permeability can be obtained in an unsaturated state of the amplifier circuit by setting the pre-amplifier to the low gain mode, while it is possible to obtain continuous measurement of the absolute value of super-low permeability of 0 to 1% by switching the mode to high gain mode.

With the fixed amplification factor amplifier adopted for AC amplification, the absolute value of permeability accurately obtained in the preceding stage can be amplified with an accurate amplification factor for calibration to permeability variation per unit voltage (for instance 0.002% per volt).

Since the biopermeability measurement apparatus itself has a calibrating function, even in the case where the gain is reduced due to contamination of the optical system, it is possible to eliminate errors of measurement by calibration prior to use.

It is therefore possible to measure permeability without urging the organism under measurement to measure slight changes in permeability under DC amplification, while it is also possible, if necessary, to measure changes only under AC amplification. Thus, the present invention can be used for the following applications.

(a) Distal blood flow variations due to shrinkage of triated muscles by nervous excitement may be measured quantitatively from time sequential data of permeability variations with time. This means that effective examination means can be provided for quantitative evaluation of self-sustaining nervous function, for which there has been no adequate means of measurement.

(b) It is possible to measure the difference of neurotic reaction of the spinal cord between the left and right sides by measuring reaction time with respect to excitement using like apparatuses for left and right hands and fingers.

(c) Regarding super-low frequency signals in DC range, all data can be measured quantitatively, and therefore conversion of time sequential data to frequency data through frequency analysis of data is possible by using a microcomputer for data processing. Therefore, even with data which involves permeability variations due to different causes and being difficult to separate with respect to time axis, in case of variations having periodicity, it is possible to obtain separation of peculiar spectra to the individual causes for analysis. With the biopermeability apparatus according to the invention, all data from DC to the upper limit of the measurement frequency range are detected and amplified, and thus it is possible to obtain frequency analysis.

(d) Frequency analysis of digital time sequential data from A/D converter using a microcomputer FFT program or the like permits detection and quantification of respiratory variation spectrum of blood flow in blood capillaries, the detection of which has been difficult in measurements with a time constant of about 1.6 sec.

What is claimed is:

1. An apparatus for measuring biopermeability comprising:
   a frame;
   light emitting means and light receiving means each secured to said frame to face each other while keeping a gap therebetween such that an organism under measurement can be received in said gap without being urged;
   preamplifier means connected to said light receiving means;
   amplifier means for zero adjustment and gain adjustment connected to an output of said preamplifier means, said amplifier means having an output for outputting data representing biopermeability;

display means for displaying biopermeability data connected between said output of said amplifier means and ground;

wherein said light emitting means is a light emitting diode; and wherein said preamplifier means is an operational amplifier having two different selectable gains, one of said selectable gains being unity gain and the other 100 times gain;

an AC inverting amplifier circuit connected to said output of said amplifier means, and including a CR coupler and an amplifier having a fixed amplification factor, said AC inverting amplifier circuit having an output for outputting AC data.

2. The apparatus as claimed in claim 1, further comprising:

data processing means connected to said output of said amplifier means and said output of said AC inverting amplifier circuit, said data processing means automatically processing data output from said amplifier means and/or data output from said AC inverting amplifier circuit, and displaying the resulting processed data.

3. The apparatus as claimed in claim 2, wherein said data processing means comprises:

means for converting the output of said amplifier means and said AC inverting circuit data into respective digital data;

means for performing frequency analysis of the digital data output from the converting means;

means for storing waveform data and frequency spectra data obtained from said frequency analysis means;

display means for displaying said waveform data and frequency spectra data; and control means for controlling the operation of said data processing means.

4. The apparatus as claimed in claim 1, wherein said amplifier means has an amplification factor of 50.

5. The apparatus as claimed in claim 1, wherein said AC inverting amplifier circuit includes an inverting amplifier connected to said output of said amplifier means, said inverting amplifier having an output for outputting said data of said AC inverting amplifier circuit.

6. The apparatus as claimed in claim 5, wherein said inverting amplifier has a unity amplification factor.

7. The apparatus as claimed in claim 1, further comprising:

switching means provided between said CR coupler and inverting amplifier to operably cause discharge of a capacitor provided in said CR coupler for zeroing the base line of measured waveforms.

* * * * *

UNITED STATES PATENT AND TRADEMARK OFFICE
CERTIFICATE OF CORRECTION

PATENT NO. : 5,144,951
DATED : September 8, 1992
INVENTOR(S) : Kazuma Uematsu, et al.

It is certified that error appears in the above-identified patent and that said Letters Patent is hereby corrected as shown below:

On the title page,

In the Abstract, line 11, change "summing: to --off-set adjustment--.

Column 4, line 7, delete "suitably".

Column 4, line 45, change "Foregoing" to --The foregoing--.

Column 5, line 16, change "organism" (second occurrence) to

--. Organism--.

Column 5, line 53, change "be" to --is--.

Column 5, line 54, change "is" to --be--.

Column 7, line 22, delete "provided".

Column 7, line 27, after "by" insert --a--.

UNITED STATES PATENT AND TRADEMARK OFFICE
CERTIFICATE OF CORRECTION

PATENT NO. : 5,144,951

DATED : September 8, 1992

INVENTOR(S) : Kazuma Uematsu, et al.

It is certified that error appears in the above-identified patent and that said Letters Patent is hereby corrected as shown below:

Column 7, line 58, change "with" (first occurrence) to --at--.

Signed and Sealed this

Second Day of November, 1993

Attest:

BRUCE LEHMAN

*Attesting Officer*  *Commissioner of Patents and Trademarks*